United States Patent [19]

Paspek et al.

[11] 4,230,888

[45] Oct. 28, 1980

[54] PROCESS FOR PURIFICATION OF ACRYLIC ACID BY FRACTIONAL CRYSTALLIZATION

[75] Inventors: Stephen C. Paspek, Cleveland; William A. Every, Twinsburg, both of Ohio

[73] Assignee: Standard Oil Company (Ohio)

[21] Appl. No.: 860,937

[22] Filed: Dec. 15, 1977

[51] Int. Cl.$^2$ .................... C07C 51/42; C07C 57/04; B01D 9/02
[52] U.S. Cl. .................................. 562/600; 260/707; 260/DIG. 35; 562/532; 562/545
[58] Field of Search ........... 260/526 N, 707, DIG. 35; 562/532, 534, 600, 535, 545-547

[56] References Cited

U.S. PATENT DOCUMENTS 3,846,488  11/1975  Otsuki .............................. 260/526 N

OTHER PUBLICATIONS

Chem. Abstracts, 48:1425f.

*Primary Examiner*—Vivian Garner
*Attorney, Agent, or Firm*—David J. Untener; Herbert D. Knudsen; Larry W. Evans

[57] ABSTRACT

Pure acrylic acid may be obtained from an aqueous solution containing acrylic acid by fractional crystallization wherein a salt is added to the aqueous solution that eliminates the eutectic point between acrylic acid and water.

12 Claims, No Drawings

PROCESS FOR PURIFICATION OF ACRYLIC ACID BY FRACTIONAL CRYSTALLIZATION

BACKGROUND OF THE INVENTION

Acrylic acid is currently manufactured by the vapor phase catalytic oxidation of propylene or acrolein. The gaseous reactor effluent from this process contains from about 10 to 80 wt.% acrylic acid, with water, acetic acid and various organic impurities. This stream is then condensed or absorbed to obtain an aqueous solution of acrylic acid, acetic acid and water.

Purification of this stream to obtain acrylic acid has been extremely difficult. The relative volatilities of acrylic acid, acetic acid and water prevents simple fractional distillation as a method of purification.

Several processes have been proposed for this purification. U.S. Pat. No. 3,816,524 describes a method of separating acrylic acid by using various solvents to extract the acrylic acid from the aqueous solution. U.S. Pat. No. 3,432,401 describes a method of using specific solvents as entrainers to aid in azeotropic distillation.

Both of these prior art processes suffer various disadvantages in that the temperatures necessary to perform distillation and solvent recovery can cause polymerization of the acid. Further, in extraction systems large amounts of solvent are necessary and such systems tend to have a high solvent loss.

As stated in U.S. Pat. No. 3,432,401, fractional crystallization has not been considered as a means for recovering acrylic acid because a eutectic between acrylic acid and water exists at 63% by volume of acrylic acid. Below the eutectic point, the acrylic acid concentrates in a liquid phase, while above the eutectic, the acid concentrates in a solid phase. The existence of the eutectic precludes complete separation of acrylic acid and water by direct fractional crystallization.

Salts have been used in the process for the recovery of acrylic acid for various purposes. U.S. Pat. No. 2,922,815 discloses that calcium chloride, sodium sulfate, and dry metal salts such as nickel chloride and nickel bromide have been used as drying agents to concentrate the acrylic acid found in the aqueous solution up to about 80%. U.S. Pat. No. 3,846,488 discloses a method for accelerating the separation of an organic solvent phase from an aqueous phase obtained by the extraction of acrylic acid with a solvent by adding an alkali metal salt or ammonium salt in minute amounts to the aqueous solution.

Rather than accelerating separation between a solvent and water, or drying the aqueous solution, it has been discovered that the addition of certain salts to the aqueous solution removes the eutectic point between acrylic acid and water thereby allowing simple fractional crystallization.

SUMMARY OF THE INVENTION

The invention is a process for separating acrylic acid from an aqueous solution containing acrylic acid comprising adding a salt that eliminates the eutectic point between acrylic acid and water to the aqueous solution in an amount sufficient to saturate said aqueous solution, and fractionally crystallizing said aqueous solution to obtain acrylic acid.

Fractional crystallization is a method of separating close boiling or azeotropic liquid mixtures. The method is a sequence of melting, partial freezing and separation stages. Often, fractional crystallization can be more economical than distillation in energy consumption because latent heats of crystallization are usually much smaller than latent heats of vaporization. A discussion of fractional crystallization may be found in *The Encyclopedia of Chemical Technology* 2nd. ed., vol. 6, page 493.

Basically, fractional crystallization can be used when two substances form a solid solution upon cooling. For example, a solution containing 50 wt.% of component A when cooled, may precipitate a solid containing 65 wt.% of component A. This solid can be separated from the liquid phase and reheated so that a liquid is formed having 65 wt.% of component A. If this liquid is recooled, a solid may participate out that has 80 wt.% of component A. As can be seen, by simply increasing the number of stages, up to 100% pure component A can be obtained. However, when two substances form a maximum or minimum melting point, a complete separation of the components is impossible. Acrylic acid and water are two such components. They form a eutectic at about 65 vol.% of acrylic acid.

It has been discovered that the addition of certain salts have the ability to eliminate this eutectic and allow fractional crystallization.

The method for determining whether a specific salt has the ability to eliminate the eutectic is relatively easy. Basically, a concentrated aqueous solution of acrylic acid and water can be saturated with the salt and then cooled until a precipitate forms. Measurement of the relative acrylic acid concentrations in the remaining liquid and solid phases at a range of compositions should provide sufficient information to determine if the eutectic has been eliminated.

One such salt that will eliminate the eutectic is sodium chloride. It is anticipated that other alkali metal salts, the halides, nitrates and sulfates thereof, and ammonium salts will also remove the eutectic. However, it has been found that barium chloride, ferric chloride, and tin chloride have no significant effect upon the acrylic acid-water solid-liquid equilibrium.

The amount of salt added to the aqueous solution should be sufficient to saturate said solution. For example, about 10 wt.% sodium chloride is required to saturate a 50 wt.% acrylic acid solution.

Although not required, after salt addition the aqueous solution should be thoroughly mixed before being sent to fractional crystallization.

The addition of the salt to the aqueous solution will depress the freezing points of the aqueous solution slightly. However, the temperatures required for fractional crystallization are industrially practical. A solution saturated with sodium chloride can be fractionally crystallized over a temperature range from about $-23°$ C. to $+14°$ C.

Another advantage obtained by the addition of salt is that the separation per stage of fractional crystallization is much greater than that of the acrylic acid/water system alone. This has the advantage of reducing the number of stages required and hence the cost for recovering acrylic acid. The fractional crystallization can be carried out in 3-6 stages.

An advantage in using a salt such as sodium chloride is that the remaining liquid from the crystallizer can be passed to an evaporator. Evaporation of the water enables the recovery and recycling of the salt.

EXAMPLE—CRYSTALLIZATION OF ACRYLIC ACID SOLUTION

Crystallization was carried in a pseudo-fluid bed crystallizer. Mixing was accomplished by the bubbling of compressed air through a fritted glass disc that comprised the bottom of the crystallizer. The air was pre-cooled by first passing it through a stainless steel coil emersed in the bath. After crystallization, the remaining liquid was withdrawn by vacuum with the dry crystals remaining on the glass disc.

Aqueous solutions with varying concentrations of acrylic acid were prepared. These solutions were then saturated with sodium chloride. The solutions were independently fed to the crystallizer, wherein crystallization took place. After separation, analysis of the liquid phase and the melted solid phase was performed by titration. The results are shown in the table below.

TABLE
CRYSTALLIZATION OF ACRYLIC ACID/WATER/NaCl

| Feed Comp. Vol. % Acrylic Acid | Freezing Pt. °C. | Vol. % Acrylic Acid Solid Phase | Vol. % Acrylic Acid Liquid Phase |
|---|---|---|---|
| 25 | −16.8 | 42.8 | 20.6 |
| 50 | −17.8 | 64.5 | 49.6 |
| 75 | −9.8 | 86.4 | 69.1 |
| 85 | −5.0 | 98.3 | 84.8 |
| 100 | 14.0 | 100 | 100 |

As can be seen in the table above, the eutectic point between acrylic acid and water has been eliminated, thereby allowing the recovery of pure acrylic acid.

It is anticipated that starting with an aqueous solution containing 50 wt.% acylic acid, that 3–5 stages of crystallization will result in 99%+acrylic acid. This product acrylic acid contains less than 0.02 wt.% sodium chloride. The saturated brine leaving the crystallizer contains about 14 wt.% sodium chloride which can be recovered by simple evaporation.

We claim:

1. A method of separating acrylic acid from an aqueous solution containing acrylic acid comprising adding a salt that eliminates the eutectic point between acrylic acid and water to the aqueous solution in an amount sufficient to saturate said aqueous solution, and fractionally crystallizing said aqueous solution to obtain acrylic acid.

2. The process of claim 1 wherein the aqueous solution containing salt is mixed prior to fractional crystallization.

3. The process of claim 1 wherein the fractional crystallization is carried out in 3–6 stages.

4. The process of claim 3 wherein the number of stages for fractional crystallization is 3–5.

5. The process of claim 1 wherein the aqueous solution is fractionally crystallized to obtain acrylic acid crystals and a brine stream containing the salt and water and the brine stream is withdrawn and evaporated to recover the salt.

6. The process of claim 1 wherein the salt is an alkali metal salt.

7. The process of claim 6 wherein the alkali metal in the salt is sodium.

8. The process of claim 7 wherein the salt is sodium chloride.

9. The process of claim 8 wherein the aqueous solution containing salt is mixed prior to fractional crystallization.

10. The process of claim 8 wherein the fractional crystallization is carried out in 3–6 stages.

11. The process of claim 8 wherein the number of stages for fractional crystallization is 3–5.

12. The process of claim 8 wherein the aqueous solution is fractionally crystallized to obtain acrylic acid crystals and a brine stream containing the salt and water and the brine stream is withdrawn and evaporated to recover the sodium chloride.

* * * * *